United States Patent [19]

Putt et al.

[11] Patent Number: 5,028,412

[45] Date of Patent: Jul. 2, 1991

[54] ORAL COMPOSITIONS COMPRISING ANTI-CALCULUS AGENTS

[75] Inventors: Mark S. Putt; Carl J. Kleber, both of Fort Wayne, Ind.

[73] Assignee: Purdue Research Foundation, West Lafayette, Ind.

[21] Appl. No.: 554,083

[22] Filed: Jul. 17, 1990

Related U.S. Application Data

[63] Continuation of Ser. No. 320,784, Mar. 9, 1989, abandoned, which is a continuation of Ser. No. 44,710, May 1, 1987, abandoned.

[51] Int. Cl.$^5$ .......................... A61K 7/16; A61K 7/18; A61K 7/22; A61K 7/24
[52] U.S. Cl. ........................................ 424/48; 424/440; 424/464; 424/49; 424/52; 424/53; 424/54; 424/55; 424/56; 424/58; 514/835; 514/901
[58] Field of Search ...................... 424/48–58, 424/464, 440; 514/835, 901

[56] References Cited

U.S. PATENT DOCUMENTS

| | | | |
|---|---|---|---|
| 4,108,981 | 8/1978 | Muhler et al. | 424/55 |
| 4,146,605 | 3/1979 | Ritchey | 424/49 |
| 4,400,372 | 8/1983 | Muhler | 424/48 |
| 4,645,662 | 2/1987 | Nakashima | 424/54 |
| 4,652,444 | 3/1987 | Maurer | 424/49 |

FOREIGN PATENT DOCUMENTS

AL829272 12/1969 Canada .
0132913 7/1985 Japan .

OTHER PUBLICATIONS

Lion Corp., Abst. of J6 0132-913-A, Lioy 21.12.83 (English Language Translation).
Sunstar, Inc., Abstract of Japanese Patent Application No. 60-26081.

*Primary Examiner*—Ronald W. Griffin
*Attorney, Agent, or Firm*—Kirkland & Ellis

[57] ABSTRACT

Anti-calculus oral compositions include an aluminum salt and an aliphatic carboxylic acid or water-soluble salt thereof capable of complexing with the aluminum, together with a carrier suitable for use in the oral cavity. Such compositions exhibit marked effectiveness in inhibiting the formation and growth of calculus on the dental enamel.

6 Claims, No Drawings

ORAL COMPOSITIONS COMPRISING ANTI-CALCULUS AGENTS

This is a continuation of co-pending application Ser. No. 07/320,784 filed on Mar. 9, 1989, now abandoned, which is a continuation of Ser. No. 07/044,710 filed on May 1, 1987, now abandoned.

BACKGROUND OF THE INVENTION

1. Field of the Invention

The present invention relates to aqueous anti-calculus oral compositions comprising certain aluminum-carboxylic acid complexes, and to methods for their use. More particularly, this invention relates to aqueous oral compositions comprising complexes of water-soluble, non-toxic aluminum salts and certain aliphatic carboxylic acids and water-soluble salts thereof.

2. Description of Prior Art

Dental research has developed substantial evidence that beyond the age of 40 years loss of teeth is predominantly the result of periodontal involvements rather than dental caries. An important factor contributing to periodontal disease is the accumulation of dental calculus (e.g., salivary tartar) on the teeth. These deposits contribute to tissue inflammation of the surrounding gingiva, and, as the condition increases in severity, the supporting bone is also affected. These reactions lead to the destruction of the supporting structures and subsequent loss of teeth.

A wide variety of chemical and biological agents have been described in the art for retarding calculus formation or for removing calculus after it is formed. Periodic mechanical removal of calcified deposits by the dentist or dental hygienist is routine dental office procedure. However, a substantial part of the population fail to obtain periodic mechanical removal of deposits, either because of the inconvenience associated with visiting a dentist or for other reasons. Thus, the subject invention has as a primary aspect the utilization of compositions comprising aluminum carboxylate complexes which exhibit surprising and unexpected effectiveness as anti-calculus agents (i.e., agents useful in reducing a tendency of oral hard tissues to accumulate dental calculus), and yet which may be safely employed in the oral cavity.

It has heretofore been suggested by Ritchey, U.S. Pat. No. 4,146,605, that certain aluminum compounds may be effective in anti-calculus compositions adapted for oral use, such as dentifrice preparations, toothpastes and chewing gum. According to the teaching of Ritchey, the aluminum should be "substantially in the ionic form." The Ritchey reference teaches that "the active constituent related to anti-calculus activity is the aluminum ion" and that "a theory explaining the action of aluminum in the present invention is that aluminum may be involved in an exchange type of reaction taken place at the surface of calculus." Compositions in accordance with Ritchey have not been effective against dental calculus, however, apparently because of their reliance on ionic aluminum as the active moiety.

The use of carboxylic acids in combination with calcined kaolin in a chewing gum has also been found to yield anti-calculus benefits. For example, in Muhler, U.S. Pat. No. 4,400,372, such a composition is described as being useful in polishing the teeth so as to remove dental calculus and prevent its reformation. The anti-calculus mechanism of the reference compound is representative of other agents that rely upon physical rather than chemical means to prevent calculus.

The present invention is predicated upon the discovery that complexes of certain aluminum salts and certain aliphatic carboxylic acids and their salts exhibit surprising anti-calculus activity, particularly in comparison to corresponding compositions having either no aluminum or uncomplexed ionic aluminum not in the presence of a complexing aliphatic carboxylic acid or a salt thereof.

Accordingly, it is a primary object of this invention to provide new and unique oral compositions characterized by the inclusion of an aluminum-carboxylate complex comprising a non-toxic aluminum salt and a complexing aliphatic carboxylic acid or water-soluble salt thereof.

A further object is to provide new methods useful in the control of dental calculus.

A still further object is to provide new compositions useful in reducing the accumulation of dental calculus on oral hard tissues.

The objects, advantages, and features of the subject invention will hereinafter appear from the following detailed description of the invention, including exemplary embodiments thereof.

SUMMARY OF THE INVENTION

The foregoing and other objects, advantages and features in accordance with the subject invention, may be achieved with anti-calculus oral compositions comprising a non-toxic amount of a water-soluble aluminum salt and a stable complexing carboxylic acid or water-soluble salt thereof at a pH suitable for use in the oral cavity. The particular water-soluble aluminum salt employed is not critical, and substantially any non-toxic, water-soluble, aluminum ion-containing salt may be used in which the aluminum is available to form the anti-calculus carboxylate complexes of the subject invention. Preferably, the stable, complexing carboxylic acid is selected from the class consisting primarily of hydroxyl and keto derivatives of aliphatic mono-, di-, and tri-carboxylic acids and water-soluble salts thereof. More specifically, the preferred complexing carboxylic acid possesses at least one hydroxyl group (or keto group) adjacent to a carboxyl group or at least two carboxyl groups separated by no more than one carbon atom. The preferred acids are citric, ascorbic, malic, glyceric, glycolic, malonic, gluconic, tartaric and tartronic acids and their water-soluble salts.

The benefits of this invention may be achieved over a wide range of aluminum to carboxylic acid ratios depending on the pH, the complexing carboxylic acid employed, and the formation of the desired complex with aluminum. The aluminum-carboxylate complexes serve to inhibit calculus formation and at the same time affect pathogenic oral microorganisms so as to reduce gingival inflammation. In its method aspect, regular use of an oral composition of the character described reduces the formation of dental calculus.

DETAILED DESCRIPTION OF THE PREFERRED EMBODIMENTS -

The anti-calculus oral compositions of this invention comprise a water-soluble complex of a non-toxic aluminum salt and a stable, complexing carboxylic acid or water-soluble salt thereof in which the presence of free aluminum ions is minimized. "Oral compositions", as used herein, means products which are used in the mouth and which contact substantially all of the dental surfaces. Such products include, for example, dentifrices, mouthwashes, chewing gums, lozenges, topical solutions, prophylaxis pastes and the like. In addition to the aqueous aluminum-carboxylic acid complexes, such oral compositions also comprise a "carrier suitable for use in the oral cavity," a term meant to include those non-toxic materials (such as cleaning and polishing agents, sudsing agents, chewing gum bases, humectants, and the like described hereinafter to be constituents of dentifrices, chewing gums, and prophylaxis pastes), as well as water and other liquids which serve as carrier vehicles in mouthwashes and topical solutions.

It is believed that the water-soluble aluminum-carboxylic acid complexes of this invention comprise aluminum in octahedral coordination with bidentate or polydentate ligands consisting of aliphatic carboxylic acids which possess at least one hydroxyl (or keto) group adjacent to a carboxyl group or at least two carboxyl groups separated by no more than one carbon atom. Coordination of carboxylates of this type, where hydroxyl and carboxyl groups are the only donors, produce bidentate and polydentate ligands that generate stable five- and/or six-member chelate rings with aluminum. It is further believed that an important feature of these complexes is that the octahedral coordination sphere is not of necessity saturated, but permits various hydrated and hydroxylated species, depending on pH, which are capable of coordinating with phosphate groups to "block" mineralization sites, resulting in their utility as effective anti-calculus agents. In contrast, a polydentate ligand such as ethylene diamine tetraacetic acid (EDTA) completely saturates the coordination sphere of aluminum and produces such a remarkably stable complex that no coordination sites are available, and thus the EDTA complex has no utility as a calculus inhibitor.

The aqueous aluminum-carboxylic acid complexes of this invention may be prepared by a variety of methods so long as aluminum ions and complexing carboxylate ions are provided in an aqueous medium at a pH in the range of about 2 to about 10. The foregoing pH range is critical in that the carboxylate complexes of this invention exist only within this pH range; below about pH 2 the hydrated aluminum species, $Al(H_2O)_6+3$, predominates and above about pH 10 the tetrahedral hydroxylated complex known as aluminate, $Al(OH)_4-$, is the major species. The preferred pH range is from about 4 to about 8 and is preferably achieved through a proper balancing of the aluminum salts and the carboxylate salts, or by the addition of an alkaline or acidic agent.

The carboxylate ligand and aluminum ion may be supplied over a wide range of molar ratios which are dependent on the pH, the complexing carboxylate used, and the concomitant formation of the desired complex with aluminum. However, benefits of this invention may be obtained at carboxylate to aluminum molar ratios lying generally in the range of about 6:1 to about 1:3.

The aluminum-carboxylate complexes may be formed by supplying aluminum and complexing carboxylate ions at the indicated levels in an aqueous medium at a pH lying in the range of about 2 to about 10. Formation of the desired complexes appears to be optimal in the pH range of about 4 to about 8. Alternatively, the desired complexes may be formed in situ during the formulation of oral compositions produced in accordance with this invention. It may be desirable to prepare the complexes and to exclude the presence of spectator ions which could adversely affect taste. Suitable preparation routes for this purpose include reacting sodium aluminate and the carboxylic acid in an aqueous medium to form the complex directly. Another method is to react aluminum sulfate and the carboxylic acid and thereafter to remove the sulfate anion by adding barium hydroxide so as simultaneously to precipitate spectator ions and adjust the pH. A still further method involves passing a solution containing spectator ions over a mixed-bed ion exchange column in order to obtain a spectator-free system. A variety of other procedures may be employed as will be obvious to those skilled in the art.

The water-soluble aluminum salt is selected from the group which provides available aluminum ions in solution for the formation of the anti-calculus carboxylate complexes of the subject invention. Suitable aluminum salts include aluminum acetate, aluminum ammonium sulfate, aluminum bromate, aluminum bromide, aluminum chlorate, aluminum chloride, aluminum iodide, aluminum lactate, aluminum nitrate, aluminum phenolsulfonate, aluminum potassium sulfate, aluminum sodium sulfate, aluminum sulfate, potassium aluminate, and sodium aluminate. Aluminum chloride and aluminum potassium sulfate are preferred by reason of their rapid solubility, wide availability, and established safety.

The stable, complexing carboxylic acids that are employed in accordance with this invention include dicarboxylic acids (e.g., malonic, methylmalonic, dimethylmalonic, and oxalic); tricarboxylic acids (e.g., carboxymalonic); alpha-hydroxymonocarboxylic acids (e.g., acetonic, ascorbic, gluconic, glyceric, glycolic, 2-hydroxybutyric, 2-hydroxyhexanoic, 2-hydroxy-2-methylbutyric, 2-hydroxy-3-methylbutyric, hydroxyvaleric, idonic, lactic and leucic); alpha-ketomonocarboxylic acids (e.g., acetylpyruvic, 2-ketobutyric, and pyruvic); alpha-hydroxydicarboxylic acids (e.g., citramalic, dihydroxymaleic, dihydroxymalic, dihydroxymalonic, dihydroxytartaric, dimethylmalic, dimethylmalonic, glucaric, hydroxyfumaric, hydroxyisosuccinic, hydroxymaleic, 2-hydroxyglutaric, malic, mucic, tartaric, and tartronic); alpha-ketodicarboxylic acids (e.g., 2-ketoadipic, 2-ketoglutaric, ketomalonic, oxalacetic, and trihydroxyglutaric); and alpha-hydroxytricarboxylic acids (e.g., citric, 1,2-dihydroxy-1,2,3-propanetricarboxylic, isocitric, and hydroxymethanetricarboxylic).

The preferred complexing carboxylic acids which may be employed in accordance with this invention are alpha-hydroxy carboxylic acids including naturally-occurring and commonly used food acids such as citric, malic, tartaric, ascorbic, glyceric, glycolic, tartronic, malonic, and gluconic.

The aluminum-carboxylate complexes in general should be provided at a level greater than 0 up to about 25% by weight of the oral composition. Increasing the amounts of the complexes to higher levels is limited by their solubility and by taste considerations.

The carboxylic acid and aluminum salt are incorporated with carriers suitable for use in the oral cavity in oral compositions such as dentifrices, prophylaxis pastes, mouthwashes, topical solutions, chewing gums, lozenges, and the like. Suitable carriers include, in the case of dentifrices and prophylaxis pastes, cleaning and polishing agents and the other constituents ordinarily provided in dentifrices and prophylaxis pastes. In the case of topical solutions and mouthwashes, suitable carriers include water and other liquids. A suitable chewing gum carrier includes any of the commercially available chewing gum bases and the other constituents ordinarily provided in chewing gums. Lozenges may employ carriers such as sorbitol, xylitol, dextrose, fructose, and the like.

The compositions discovered by applicant herein exhibit substantial effectiveness in inhibiting both the initiation of calcification and mineralization of dental calculus on the oral hard tissues. The anti-calculus activity of the compositions is substantially and surprisingly greater than is attainable with aluminum ions in the absence of a complexing carboxylic acid, as is disclosed in the prior art.

It is now believed that calculus formation occurs when salivary calcium and phosphate mineralize the phosphoproteolipid material in the matrix of the plaque deposits on the teeth at the gingival margin. In accordance with the present invention, but without limiting the invention, it is believed that the aluminum-carboxylic acid complex of the oral composition coordinates with the phosphates on the phosphoproteolipids and thereby "blocks" the sites at which mineralization might otherwise begin. The extent to which this mechanism is successful in preventing the initiation of calcification is dependent in large part, upon the degree to which the aluminum-carboxylate complex "blocks" the site. Because release of the anti-calculus actives and consequent blocking of mineralization sites appears to be time dependent, it has been found that increasing contact time of the oral composition in the mouth dramatically increases calculus inhibition. Accordingly, increasing the residence time of the oral composition in the mouth by, for example, utilizing a chewing gum, or lozenge carrier, is preferred.

DENTIFRICE COMPOSITIONS

Oral compositions adapted for regular home use, such as dentifrice compositions and the like, typically comprise about 10 to about 95% by weight, of a cleaning and polishing agent as a carrier suitable for use in the oral cavity. Various cleaning and polishing agents suitable for use in dentifrice compositions include purified, calcined kaolins as described in Muhler, et al., U.S. Pat. No. 4,122,163, mixtures of calcined kaolin and talc as taught in Muhler, et al., U.S. Pat. No. 4,428,928, aluminum silicates, zirconium silicate, precipitated silicas, silica gels, aluminas, insoluble metaphosphates and pyrophosphates, and mixtures thereof. Another class of abrasives suitable for use herein are the particulate, thermosetting, polymerized resins, including, for example, melamines, phenolics, ureas, melamine-ureas, urea-formaldehydes, cross-linked epoxides and cross-linked polyesters. The preferred abrasives are purified, calcined kaolins.

A minor but effective and non-toxic amount of a fluoride compound, usually within a range sufficient to supply from about 0.01 to about 1.0 percent (preferably about 0.1 percent) fluoride ion may also be provided in the composition to render it anticariogenic. Fluoride compounds which supply fluoride ions in aqueous solution and which thus are suitable for use in the oral compositions of this invention are well known in the art. Examples of such compounds are water-soluble fluoride salts such as sodium fluoride, stannous fluoride, and sodium monofluorophosphate. Other suitable adjuvants include aluminum fluoride, stannic fluoride, potassium fluoride, zinc fluoride, indium fluoride, lead fluoride, iron fluoride, ammonium fluoride, as well as more complex adjuvants such as fluorosilicates, fluorozirconates, fluorostannites, fluoroborates, fluorotitanates, fluorogermanates, and various organic fluorides. Mixtures of suitable fluoride adjuvants may also be utilized. Sodium monofluorophosphate and sodium fluoride are preferred.

The pH of the compositions herein is in the range from about 2 to about 10, preferably from about 4 to about 8. The pH is preferably achieved through a proper balancing of the aluminum salts and the carboxylic acid salts or by the addition of an alkaline or acidic agent.

Cationic antibacterial agents may also optionally be added to compositions of the present invention. Suitable agents include, among others, quaternary ammonium compounds, such as benzethonium chloride and cetylpyridinium chloride, and biguanides, such as chlorhexidine, alexidine, hexetidine, and polyhexamethylene biguanide hydrochloride. These agents may be used in effective amounts ranging from about 0.01 to about 5 percent by weight of the dentifrices.

The dentifrice compositions are prepared in a conventional manner and usually will include additional ingredients to render the overall composition commercially acceptable to consumers.

Toothpastes require a binder substance to impart desired textural properties. Natural gum binders such as xanthan, tragacanth, karaya, arabic, guar, and the like and seaweed derivatives such as carragheen and alginates, and water-soluble cellulose derivatives, such as hydroxyethyl cellulose and sodium carboxymethyl cellulose can be used for this purpose. Desirably, those materials are employed which are most compatible with fluoride ion and the aluminum-carboxylic acid complexes of this invention. Binders which have no ionic groups, such as hydroxyethyl cellulose are especially preferred. Improvements in texture can also be attained by including an additional material such as colloidal magnesium aluminum silicate, fumed silica, or the like. Thickening agents in an amount of from about 0.5 to about 5.0 percent by weight can be used to form a satisfactory toothpaste.

Toothpastes conventionally contain organic surface-active agents, which may be anionic, cationic, non-ionic or ampholytic in nature. Suitable sudsing agents include, but are not limited to, water-soluble alkyl sulfates having from about eight to about 18 carbon atoms in the alkyl radical, such as sodium lauryl sulfate, water-soluble salts of sulfonated monoglycerides of fatty acids having from about 10 to about 18 carbon atoms in the alkyl radical such as sodium coconut monoglyceride sulfonate, salts of fatty acid amides of taurines such as sodium-N-methyl palmitoyl taurine, and salts of fatty acid esters of isethionic acid. Other particularly suitable surface-active materials include non-ionic agents such as condensates of sorbitan monostearate and ethylene oxide, copolymers of the poly(oxypropylene)-poly(oxyethylene) type and amphoteric agents such as quaternized imidazole derivatives. Useful cationic surface-active germicides and antibacterial compounds include tertiary amines containing one fatty alkyl group and two poly(oxyethylene) groups, benzyldimethyl stearyl ammonium chloride, and di-isobutylphenoxyethoxyethyl dimethyl benzyl ammonium chloride. Surface-active agents can be used in compositions of this invention in an amount of from about 0.5 percent to about 5.0 percent by weight of the total composition.

It is also desirable to include some humectant material in a toothpast to keep it from hardening. Materials commonly used for this purpose include glycerin, sorbitol, and other edible polyhydric alcohols. The humectants can comprise up to 80 percent of the toothpaste composition.

Flavoring materials may be included in toothpaste formulations including small amounts of oils of spearmint, wintergreen and peppermint or other natural or synthetic flavors, and sweetening agents such as saccharin, cyclamate, aspartame, dextrose, and levulose.

Preferred dentifrice preparations are given hereinafter by way of example, but it should be understood that such examples are presented for purposes of illustration, but not of limitation.

EXAMPLE I

Dentifrice

| Constituent | Parts by Weight (%) |
| --- | --- |
| Aluminum chloride | 1.21 |
| Sodium tartrate | 1.47 |
| Sodium monofluorophosphate | 0.76 |
| Polyhexamethylene biguanide (20%) | 0.50 |
| Purified, calcined kaolin | 24.00 |
| Aluminum silicate | 7.00 |
| Talc | 7.00 |
| Distilled water | 21.83 |
| Glycerin | 7.00 |
| Sorbitol (70%) | 24.00 |
| Sodium carboxymethyl cellulose | 1.35 |
| Magnesium aluminum silicate | 0.78 |
| Sodium lauryl sulfate | 1.50 |
| Sodium sacccharin | 0.40 |
| Preservatives | 0.20 |
| Flavor | 1.00 |

EXAMPLE II

Dentifrice

| Constituent | Parts by Weight (%) |
| --- | --- |
| Aluminum sulfate | 7.52 |
| Sodium citrate | 7.35 |
| Sodium monofluorophosphate | 0.76 |
| Purified, calcined kaolin | 33.00 |
| Deionized water | 13.64 |
| Glycerin | 7.00 |
| Sorbitol (70%) | 24.00 |
| Sodium carboxymethyl cellulose | 1.60 |
| Magnesium aluminum silicate | 0.78 |
| Sodium lauryl sulfate | 1.50 |
| Sodium hydroxide (q.s. to pH 7) | — |
| Sodium saccharin | 0.40 |
| Preservatives | 0.20 |
| Flavor | 1.50 |

Dentifrice preparations formulated in the foregoing manner are suitable for frequent application to teeth (e.g., as often as several times per day). When used in this manner, a new and useful method is provided for the control of dental calculus.

CHEWING GUM COMPOSITIONS

Conventional chewing gum manufacturing techniques are used in preparing regular and sugarless chewing gums and no process variations need be made.

Suitable chewing gum bases may be obtained from commercial suppliers. Suitable raw materials for gum bases which may be employed in accordance with this invention include chicle, latex, RBH resin, ester gum, petroleum waxes, resins, crown gum, Malsa compound, PU-C, picllylite resin, candelilla wax, chiquibil gum, polyvinyl acetate, styrene butadiene and the like. Suitable conventional stick gum bases include "Paloja T"; "Firm Paloja T"; and "Nova T." Suitable bubble gum bases include "Paloja Bubble T"; "Ladco Bubble T"; and "Grande Bubble T." All of these bases are commercially available from the L.A. Dreyfus Corporation, P.O. Box 500, South Plainfield, N.J. 07080. The gum base is normally employed at a level of about 10–60 percent of total gum weight. Advantageously, the gum base is about 15–30%, preferably about 18–26%, of the overall gum composition.

In addition to the aluminum-carboxylic acid complex and gum base, as described, chewing gums in accordance with this invention comprise excipients such as corn syrup, sucrose, sorbitol, xylitol and other flavoring and sweetening agents as well as various inert filler materials. In accordance with this invention, it is preferred that the gums be formulated without sucrose or other cariogenic sweetening agents. Such gums may be prepared in several possible forms such as conventional stick gum, bubble gums and the like.

The excipient constituents of the gum may include any of the conventional flavoring and sweetening components to a level in the range of about 30–80% by total gum weight. Flavors such as spearmint, peppermint, wintergreen, fruit flavors, and the like may be used. The preferred gum compositions employ non-cariogenic sweetening systems using natural and synthetic sweetening agents rather than corn syrup and sugar because of the cariogenic potential of natural sweeteners.

Inert filling ingredients, such as talc, sorbitol, mannitol, glycerin, lecithin, or the like are provided in the gum base in order to contribute to the over-all consistency of the composition.

The foregoing gum bases, excipients, and fillers are all known chewing gum constituents and are provided at conventional levels and therefore per se form no part of the present invention.

Preferred oral compositions are given hereinafter by way of example, but it should be understood that such examples are presented for purposes of illustration, but not of limitation.

EXAMPLE III

Chewing Gum

| Constituent | Parts by Weight (%) |
| --- | --- |
| Aluminum sulfate | 5.01 |
| Sodium citrate | 4.90 |
| Deionized water | 7.00 |
| Sodium hydroxide (q.s. to pH 7) | 0.85 |
| Styrene-butadiene gum base (talc filler) | 30.00 |
| Glycerol monostearate | 0.20 |
| Sorbitol powder | 50.83 |
| Flavor | 1.20 |

EXAMPLE IV

Mouthwash

| Constituent | Parts by Weight (%) |
| --- | --- |
| Aluminum nitrate | 1.88 |
| Tartronic acid | 0.69 |
| Water | 71.33 |
| Ethanol | 12.00 |
| Sodium hydroxide (q.s. to pH 6) | — |

-continued

| Constituent | Parts by Weight (%) |
| --- | --- |
| Glycerin | 13.00 |
| Sodium lauryl sulfate | 0.40 |
| Polyoxyethylene 20 sorbitan monostearate | 0.30 |
| Sodium saccharin | 0.20 |
| Flavor, color | 0.20 |

EXAMPLE V

Prophylaxis Paste

| Constituent | Parts by Weight (%) |
| --- | --- |
| Aluminum potassium sulfate | 9.48 |
| Glyceric acid | 2.12 |
| Calcined sepiolite (U.S. Pat. No. 4,418,053) | 40.00 |
| Deionized water | 13.80 |
| Glycerin | 15.00 |
| Sorbitol (70%) | 16.00 |
| Hydroxyethyl cellulose | 0.90 |
| Sodium lauryl sulfate | 1.00 |
| Sodium hydroxide (q.s. to pH 4.5) | — |
| Sodium saccharin | 0.50 |
| Preservatives | 0.20 |

EXAMPLE VI

Lozenge

| Constituent | Parts by Weight (%) |
| --- | --- |
| Aluminum chloride | 0.67 |
| Sodium ascorbate | 0.99 |
| Sorbitol | 81.00 |
| Dextrose | 15.00 |
| Magnesium stearate | 1.50 |
| Flavor, color | 0.84 |

EXPERIMENTAL EVALUATIONS

The effectiveness of anti-calculus compositions obtained in accordance with the present invention has been demonstrated by in vitro studies. In addition, the calculus inhibitory effectiveness of both chewing gums and dentifrices in accordance with this invention have been evaluated in vivo in both rat and human clinical studies.

1. Laboratory Studies

The calculus inhibiting characteristics of experimental and commercial dentifrices have been evaluated in vitro using a device (the "Calculus Machine") that simulates the oral cavity. The Calculus Machine comprises a metal base and a vertical support at each end. An electric motor and speed reduction gear box are bolted to one support and drive a plastic rod, which extends to the other support, at a constant speed of 1 rpm. Threaded holes, into which are screwed tooth specimens, are spaced at regular intervals along the length of the plastic rod. The specimens are rotated through saliva in a plastic reservoir which is sealed from the atmosphere by means of a rubber gasket.

Excised, bovine permanent incisors were trimmed, then mounted in 1.5 cm-square blocks using self-curing denture acrylic. A plastic screw was placed in the back of each block during mounting for attachment to the plastic rod. Lamellae and surface irregularities on the labial surface were reduced using a diamond grinding disk, then prophied with an aqueous slurry of pumice.

Saliva was collected each day (except weekends) in disposable plastic cups from laboratory personnel using paraffin as a stimulant. Fresh saliva was placed in the reservoir each day after the specimens were rinsed by revolving through distilled water for 2 minutes, followed by treatment, and another 2-minute water rinse. The Calculus Machine was maintained at 37° C. in an incubator for 4 weeks except during daily saliva changes and treatment.

Approximately 25 ml of the experimental solution was poured into one compartment of a segmented reservoir. Into the other compartment was poured distilled water. The 8 specimen teeth for each reservoir were revolved through the solutions at room temperature for 5 minutes each day. After treatment, the specimens were revolved through distilled water for 2 minutes in their individual compartments so as to prevent cross-contamination. The pH of the experimental solutions was adjusted by means of sodium hydroxide solutions.

At the completion of the 4-week test period, the specimens were carefully unscrewed from the plastic rod and allowed to air-dry. The deposits were meticulously removed from the enamel surface of each specimen with a dental scaler onto weighing paper and individually weighed by means of an electronic analytical balance. Physical analyses of the calculus deposits from the specimens were performed subsequently in order to determine the percentage calcified.

A summary of the calculus deposit weight for experiments involving different aluminum-carboxylate treatment groups is provided in Table 1. In nine separate experiments the aluminum-carboxylate complexes caused significant reductions in calculus deposition and calcification relative to a water control.

2. Animal Studies

In addition to the foregoing in vitro laboratory studies demonstrating the characteristics of the present invention, two rat studies were conducted in order to determine the ability of the aluminum-carboxylate complexes in accordance with this invention to inhibit the formation of dental calculus on the teeth.

Using a balanced, complete block test design, weanling rats were randomly distributed, one from each litter per group, into equivalent treatment groups of 20 according to sex and body weight. The rats were fed a calculus-producing diet for three weeks, during which time they were treated daily for five days weekly with the appropriate solution or dentifrice. The treatments were applied with a cotton swab to each molar quadrant for 15 seconds. At the end of the treatment period, the rats were sacrificed and graded for calculus accumulation. The data were analyzed by analysis of variance using a litter-matching technique to reduce experimental error and by a simultaneous significance test for multiple comparisons.

Dental calculus was scored by an estimation of the enamel surface area covered and the thickness of the deposits in accordance with the method described by M.D. Francis and W.W. Briner (J. Dent. Res. 48:1185-95, 1969). The method is based on assigning areas to each molar of both the maxillary and mandibular quadrants, where each quadrant has eleven areas bound by sulci or interproximal spaces between molars. Each animal, then, has 44 surface grades, each with a severity value from 0 to 3 as follows:

0 = No calculus

1 = Barely detectable (but an authentic deposit of hard calculus) to 25% of the area thinly covered.

2=25-75% of area covered, but not thick.

3=50-100% of area covered with a thick, heavy deposit.

A binocular microscope at 20× magnification was used, and the calculus accumulations were drawn on a calculus-scoring chart. The calculus scores are reported as the total severity score per animal (maximum=132).

In the first study, the groups with their corresponding treatments were as follows:

Group 1: Distilled water (control).

Group 2: Calcined kaolin-talc dentifrice formulation without active agents at pH 7 (placebo).

Group 3: Calcined kaolin-talc dentifrice formulation containing 0.05M aluminum chloride-citrate complex and 0.76% sodium monofluorophosphate at pH 4.3.

Group 4: Same as Group 3 at pH 7.

A summary of the dental calculus scores for all rats is provided in Table 2. Statistically significant reductions in dental calculus accumulation, relative to a water-treated control group (Group 1) and a calcined kaolin-talc placebo dentifrice group (Group 2), were observed for both experimental dentifrices (Groups 3 and 4). More specifically, significant calculus inhibitory activity was produced by aluminum chloride-citrate containing dentifrices at both pH 4.3 and 7. Comparisons between treatment groups demonstrated that both dentifrice formulations containing the aluminum-citrate complex were statistically equivalent to each other in their anti-calculus efficacy.

In the second study, the groups with their corresponding treatments were as follows:

Group 1: Distilled water (control).

Group 2: Colgate—dicalcium phosphate-based dentifrice containing sodium monofluorophosphate (commercial placebo).

Group 3: Calcined kaolin-talc dentifrice formulation containing 0.05M aluminum chloride-citrate complex and 0.76% sodium monofluorophosphate at pH 4.3.

Group 4: Aqueous solution containing 0.05M aluminum chloride-citrate complex and 0.76% sodium monofluorophosphate at pH 4.3.

Group 5: Same as Group 3 except aluminum-citrate complex at concentration of 0.25M.

The calculus scores for the second rat study are also summarized in Table 2. All treatment groups had significantly less calculus accumulation than the water control (Group 1) and the commercial placebo (Group 2). More specifically, significant calculus inhibitory activity was produced by pH 4.3 complexes of aluminum chloride and sodium citrate in an aqueous solution and at two concentrations in dentifrice formulations. The three groups treated with aluminum-citrate systems were statistically equivalent to each other.

No adverse reactions due to treatment were observed in any animals. Rats in all groups in both studies experienced normal weight gains that were statistically equivalent.

3. Human Study

A human clinical study was also performed in order to determine the ability of an aluminum-carboxylate complex in accordance with this invention to inhibit calculus formation.

A total of 52 adults volunteered for the study from a population previously identified as relatively rapid calculus formers. Based on their baseline calculus and gingivitis scores, the participants were distributed into two equivalent groups. After receiving a dental prophylaxis of their mandibular incisors, they were issued chewing gum, dentifrice, and a toothbrush. The experimental group was given a chewing gum containing an aluminum-citrate complex comprising as actives 5.0% aluminum sulfate and 4.9% sodium citrate at neutral pH and a dentifrice containing an aluminum-citrate complex comprising 7.5% aluminum sulfate, and 7.4% sodium citrate at pH 4.2. The control group was given a placebo chewing gum identical to the experimental gum without the actives and a commercial placebo dentifrice (i.e. Colgate). All participants were instructed to chew the gum for at least 5 minutes six times per day and to brush twice a day for a minute each time.

At the end of a four-month trial period, all subjects were examined for calculus using the Calculus Surface Index (C.S.I.) method of Ennever et al. (J. Periodontol 32:54, 1961). The C.S.I. method is based on the examination of sixteen surfaces—two proximals (scored from the lingual aspect), one labial, and one lingual—of the four mandibular incisors. The total number of surfaces on which calculus is detected (maximum of sixteen) is the subject's calculus score. The quantity of calculus on each of these surfaces is assessed on a severity scale from 0 to 3 (maximum possible score is 48) and is referred to as the Calculus Surface Severity Index (C.S.S.I.)

All subjects were also examined for gingival inflammation, which was determined using a modification of the P.M.A. Index. (See M. Massler, I. Schour and B. Chopra: J. Periodontol 21:146, 1950). The modified P.M.A. Index is based on the examination of the gingival tissue surrounding the four mandibular incisors. The degree of inflammation for each gingival unit is assessed as described by M. Massler (J. Periodontol 38:592, 1967).

The mean scores from the trial period of this study for both the Calculus Surface Index (C.S.I.) and the Calculus Surface Severity Index (C.S.S.I.) are summarized according to treatment group in Table 3. Table 3 also provides the mean gingivitis scores according to treatment group. The data reported in Table 3 demonstrate highly significant reductions of approximately 40% in both calculus accumulation and gingival inflammation of the experimental group relative to the control group.

Analysis of the rate of release of the actives during chewing of the experimental gum demonstrated that more than 60% of the aluminum was released within the first minute and approximately 90% after 5 minutes of chewing.

From the foregoing it can be seen that the oral compositions in accordance with this invention have the ability to substantially inhibit the formation and growth of calculus on the dental enamel. In combination with other recommended oral hygiene techniques (e.g. daily toothbrushing and periodic professionally administered prophylaxis treatments), use of the oral compositions of this invention substantially enhance the overall oral health of the user.

TABLE 1

CALCULUS MACHINE STUDIES

| Treatment Solution | Solution pH | Calculus Weight Mean ± S.E. (mg) | Reduction (%) | Percent Calcified |
|---|---|---|---|---|
| *Experiment 1* | | | | |
| Distilled water | — | 4.61 ± 0.20 | — | 26 |
| 0.02 M Al tartrate complex | 7.0 | 2.72 ± 0.08 | 41 | 13 |
| *Experiment 2* | | | | |
| Distilled water | — | 5.08 ± 1.25 | — | 59 |
| 0.02 M AlCl$_3$ - 0.03 M malate complex | 7.0 | 1.35 ± 0.13 | 73 | 38 |
| *Experiment 3* | | | | |
| Distilled water | — | 2.50 ± 0.14 | — | 28 |
| 0.02 M AlCl$_3$ - 0.03 M tartrate complex | 7.0 | 1.90 ± 0.20 | 24 | 22 |
| *Experiment 4* | | | | |
| Distilled water | — | 2.36 ± 0.37 | — | 59 |
| 0.02 M AlCl$_3$ - 0.03 M malate complex | 7.0 | 1.40 ± 0.10 | 42 | 23 |
| *Experiment 5* | | | | |
| Distilled water | — | 3.13 ± 0.39 | — | 41 |
| 0.05 M AlCl$_3$ - 0.06 M tartrate complex | 7.0 | 1.52 ± 0.17 | 51 | 30 |
| *Experiment 6* | | | | |
| Distilled water | — | 2.65 ± 0.32 | — | 42 |
| 0.01 M AlCl$_3$ - tartrate complex | 7.0 | 1.80 ± 0.32 | 32 | 38 |
| 0.05 M AlCl$_3$ - 0.06 M tartrate complex | 7.0 | 0.91 ± 0.12 | 66 | 14 |
| *Experiment 7* | | | | |
| Distilled water | — | 3.09 ± 0.21 | — | 61 |
| 0.05 M AlCl$_3$ - citrate complex | 4.3 | 0.14 ± 0.07 | 96 | 16 |
| *Experiment 8* | | | | |
| Distilled water | — | 2.31 ± 0.13 | — | 64 |
| 0.05 M AlCl$_3$ - citrate complex | 7.0 | 0.11 ± 0.03 | 95 | 56 |
| *Experiment 9* | | | | |
| Distilled water | — | 2.41 ± 0.12 | — | 66 |
| 0.025 M Al$_2$(SO$_4$)$_3$ - citrate complex | 4.3 | 0.15 ± 0.03 | 94 | 42 |

TABLE 2

SUMMARY OF RAT CALCULUS STUDIES

| Group | Treatment | Calculus Score* | Reduction |
|---|---|---|---|
| | *Study 1* | | |
| 1 | Distilled water control | 82.90 ± 3.64 | — |
| 2 | Placebo dentifrice | 87.79 ± 4.12 | −5.9 |
| 3 | Dentifrice containing 0.05 M Al-citrate complex at pH 4.3 | 56.63 ± 2.88 | 31.7 |
| 4 | Dentifrice containing 0.05 M Al-citrate complex at pH 7.0 | 65.42 ± 3.23 | 21.1 |
| | *Study 2* | | |
| 1 | Distilled water control | 94.10 ± 2.83 | — |
| 2 | Commercial placebo dentifrice | 98.45 ± 3.03 | −4.6 |
| 3 | Dentifrice containing 0.05 M Al-citrate complex at pH 4.3 | 77.40 ± 2.74 | 17.7 |
| 4 | Aqueous solution containing 0.05 M Al-citrate complex at pH 4.3 | 70.55 ± 3.56 | 25.0 |
| 5 | Dentifrice containing 0.25 M Al-citrate complex at pH 4.3 | 71.30 ± 2.98 | 24.2 |

*Mean ± standard error.

TABLE 3

SUMMARY OF CALCULUS AND GINGIVITIS SCORES FROM HUMAN STUDY

| Group | Calculus Scores* | | Gingivitis Scores* |
|---|---|---|---|
| | C.S.I. | C.S.S.I. | P.M.A. Index |
| Control | 13.48 ± 0.49 | 16.60 ± 1.30 | 4.72 ± 0.95 |
| Experimental | 8.44 ± 1.15 | 8.83 ± 1.29 | 2.68 ± 0.63 |
| Reduction (%) | 37.4 | 46.8 | 43.2 |

*Mean ± standard error.

We claim:

1. An anti-calculus oral composition consisting essentially of:

an aluminum-carboxylate complex comprising a water-soluble, nontoxic aluminum salt and an aliphatic carboxylic acid or water-soluble salt thereof selected from the group consisting of citric, ascorbic, malic, glyceric, glycolic, malonic, gluconic, tartaric and tartronic acids and salts thereof, wherein carboxylic acid or salt thereof and the aluminum salt are provided in a molar ratio lying in the range of about 6:1 to about 1:3; and a carrier suitable for use in the oral cavity, the composition having a pH in the range of about 2 to about 10; the composition being substantially free from ionic aluminum; and the aluminum-carboxylate complex being present in an amount ranging from greater than zero up to about 25% by weight of the composition.

2. An anti-calculus oral composition, as claimed in claim 1, wherein said carrier therein is a dentifrice, chewing gum, prophylaxis paste, mouthwash, lozenge or topical solution.

3. An anti-calculus oral composition consisting essentially of:

an aluminum-carboxylate complex comprising a water-soluble, nontoxic aluminum salt and an aliphatic carboxylic acid or water soluble salt thereof selected from the group consisting of citric, ascorbic, malic, glyceric, glycolic, malonic, gluconic, tartaric and tartronic acids and salts thereof, wherein carboxylic acid or salt thereof and the aluminum salt are provided in a molar ratio lying in the range of about 6:1 to about 1:3;

an effective amount of a fluoride compound; and a carrier suitable for use in the oral cavity, the composition having a pH in the range of about 2 to about 10; the composition being substantially free from ionic aluminum; and the aluminum-carboxylate complex being present in an amount ranging from greater than zero up to about 25% by weight of the composition.

4. An anti-calculus oral composition, as claimed in claim 1, wherein the aluminum salt is aluminum sulfate and wherein the salt of a carboxylic acid is sodium citrate.

5. A chewing gum capable of inhibiting the formation of calculus on the teeth consisting essentially of a chewing gum base and an aluminum-carboxylate complex comprising a water soluble, nontoxic aluminum salt and an aliphatic carboxylic acid or water-soluble salt thereof selected from the group consisting of citric, ascorbic, malic, glyceric, glycolic, malonic, gluconic, tartaric and tartronic acids and salts thereof, wherein carboxylic acid or salt thereof and the aluminum salt are provided in a molar ratio lying in the range of about 6:1 to about 1:3; the chewing gum has a pH in the range of about 2 to about 10; the chewing gum is substantially free from ionic aluminum; and the aluminum-carboxylate complex is present in an amount ranging from greater than zero up to about 25% by weight of the chewing gum.

6. A method for inhibiting the formation of dental calculus comprising the application to the oral hard tissues of an anti-calculus oral composition as claimed in claim 1.

* * * * *